(12) United States Patent
Desjonqueres

(10) Patent No.: US 8,367,650 B2
(45) Date of Patent: Feb. 5, 2013

(54) OIL COMPOSITION BASED ON PEROXIDISED LIPIDS, WHICH CAN BE USED IN THE TREATMENT OF XEROSTOMIA

(75) Inventor: Stéphane Desjonqueres, Maisons-Laffitte (FR)

(73) Assignee: Laboratoires Carilene, Montesson (FR)

(*) Notice: Subject to any disclaimer, the term of this patent is extended or adjusted under 35 U.S.C. 154(b) by 1375 days.

(21) Appl. No.: 10/538,835

(22) PCT Filed: Dec. 22, 2003

(86) PCT No.: PCT/FR03/03861
§ 371 (c)(1),
(2), (4) Date: Jun. 13, 2005

(87) PCT Pub. No.: WO2004/058138
PCT Pub. Date: Jul. 15, 2004

(65) Prior Publication Data
US 2006/0078620 A1    Apr. 13, 2006

(30) Foreign Application Priority Data
Dec. 23, 2002 (FR) ...................... 02 16517

(51) Int. Cl.
*A61K 31/33* (2006.01)

(52) U.S. Cl. ...................................... 514/183

(58) Field of Classification Search ............... 514/183
See application file for complete search history.

(56) References Cited

U.S. PATENT DOCUMENTS
5,254,585 A * 10/1993 Desjonqueres ............... 514/552

FOREIGN PATENT DOCUMENTS
| EP | 225832 | 6/1987 |
| EP | 1077061 | 2/2001 |
| FR | 2705568 | 12/1994 |

OTHER PUBLICATIONS
English Translation of Desjonqueres (EP 1077061).*

* cited by examiner

*Primary Examiner* — Brandon Fetterolf
*Assistant Examiner* — Christopher R Stone
(74) *Attorney, Agent, or Firm* — Ladas & Parry LLP

(57) ABSTRACT

The invention relates to an oily pharmaceutical composition based on peroxidized lipids and on silica, characterized in that it contains, as essential constituents, peroxidized lipids which have a degree of peroxidation of between 5 and 600 milliequivalents per kilogram, and silica which is dispersed within said peroxidized lipids at a concentration of greater than or equal to 0.5% by weight and less than 4% by weight with respect to the weight of said composition. In this composition, the peroxidized lipids are preferably obtained by peroxidation of a natural plant oil and the silica is preferably colloidal silica. The invention also relates to the use of the composition for the preparation of a pharmaceutical composition which is intended for treating xerostomia.

33 Claims, No Drawings

OIL COMPOSITION BASED ON PEROXIDISED LIPIDS, WHICH CAN BE USED IN THE TREATMENT OF XEROSTOMIA

This application is a filing under 35 USC 371 of PCT/FR2003/003861 filed Dec. 22, 2003.

BACKGROUND OF THE INVENTION

The present invention relates to a novel composition based on peroxidised lipids which can be used notably in the treatment of xerostomia.

Xerostomia is a well known pathology which manifests itself as a sensation of dryness of the mouth.

This pathology in general results from a sluggishness or of a definitive damage of the salivary glands which causes this phenomenon.

This inconvenient syndrome may become particularly incapacitating. A sensation of burning and of pain diffuses into the buccal cavity which hinders the patient considerably from eating or drinking.

The manifestations of xerostomia can be seen most often after a long-term treatment with neuroleptics, a treatment by irradiation or chemotherapy, or in the case of immunodeficiency.

No satisfactory treatment exists at the moment, but only some products which act on the symptoms by increasing salivary secretion, in replacing the saliva, or by stimulating the salivary glands. The main treatment which is used at the moment consists of using artificial saliva or saliva substitutes which are sprayed into the mouth.

In general, these products are swallowed without much therapeutic remanence.

Many saliva substitutes are thus marketed.

The formulation of the saliva substitutes usually tends to come close to the composition of natural saliva.

Products are also known which are intended to stimulate the salivary glands.

These are in general chewing gum products or pastilles.

Various peroxidised lipids are known which are notably obtained by peroxidation of natural plant oils. The following patents will be cited in particular: BSM (in French <<Brevet Spécial de Médicament>>, <<French Special Medicine Patent>> in English) N°2 330 M, EP-A-293 535, FR-A-2 591 112, EP-A-225 831, EP-A-225 832, EP-A-225 833, EP-A-226 506, FR-A-2 461 744, FR-A-2 539 142 and EP-A-117 962, which relate either to the preparation of such peroxidised lipids, or to their applications in various fields, particularly in the treatment of certain diseases in the field of rheumatology or traumatology, or even as a healing product.

The use of peroxidised lipids has also been described in European Patent Application EP 1 077 061 in the treatment or prevention of wounds and of inflammations of the mucous membranes of the buccal cavity.

Within the context of his research work on novel means of treating dry mouth syndrome, the inventor of the present invention has now discovered that peroxidised lipids, provided that they are formulated in a form of a composition which is compatible with an application as a spray, could be used in a particularly effective manner in the treatment of xerostomia, this formulation as a spray enabling the whole of the buccal cavity and the tongue to be lined by a simple vaporisation of said composition in the mouth.

It has thus now appeared that provided the peroxidised lipids are formulated in the form of a composition which has a well determined viscosity, linked to the presence of silica in well-determined proportions in the composition, it was possible to line the whole of the mucous membranes of the mouth in a particularly simple and effective manner by means of a dosing pump, and this led to the formation of a film lining the whole of the mucous membranes and causing a real action of lubrication of the mucous membranes of the mouth.

This type of composition and mode of action proves to be particularly interesting, at a time when means of treatment are particularly sought after which are as little aggressive as possible for the organism. Further, they enable the regulation of the European Community to be satisfied in relation to medical devices.

Furthermore, it will be noted that amongst the documents cited above describing compositions based on peroxidised lipids, a certain number of them exist which cite compositions which contain colloidal silica. However, in all of these documents which cite mixtures of peroxidised lipids and colloidal silica, viscous compositions are sought after which have the consistency of an oily gel which can be applied on the skin and the mucous membranes.

These gels still contain colloidal silica concentrations of greater than 4% by weight, and in general of greater than 6% by weight. Such compositions would not enable the function sought after according to the present invention to be fulfilled, wherein it is sought to line the mucous membranes of the buccal cavity totally by vaporising the composition in the form of a spray.

SUMMARY OF THE INVENTION

The invention thus relates, as a novel product, to compositions based on peroxidised lipids and colloidal silica in well-determined proportions, as well as to the uses of these compositions.

Thus, the invention proposes a composition based on peroxidised lipids which can be diffused easily in spray form into the buccal cavity and is neither a substitute nor a stimulant of saliva. Rather, it is a buccal lubricating agent endowed with a property of adherence to the buccal mucous membrane, forming a protective film over the whole of the mucous membranes of the mouth.

The lipid film which forms avoids the loss of moisture of the buccal tissues, thus reducing the tendency of dryness of the buccal mucous membrane in patients having a reduction in the salivary function.

These properties confer notable advantages to the use of the composition as a spray based on peroxidised lipids in patients suffering from buccal dryness.

More specifically, the compositions of the present invention contain silica as thickening agent, as do the preferred compositions described in the Patent EP 1 077 061.

However, the viscosity of the compositions of the present invention is lower, so as to enable its use as a buccal spray and not as a buccal gel.

Thus, the gels described in the Application EP 1 077 061 are particularly indicated in the case in which a use is sought as a topical gel for the symptomatic relief of buccal ulcerations, gingivites and pain following wearing dental apparatuses, whereas the novel compositions according to the invention have, due to their low viscosity, the possibility of being used for lining the whole of the buccal cavity, and this leads to a novel indication of the peroxidised lipids in the treatment of xerostomia.

A more particular advantage of the compositions according to the invention is that they do not induce any pharmacological, metabolic or immunological effect, since they do not contain any pharmacological compounds and are essentially constituted of oxidised glycerol triesters and silicon dioxide, the other constituents being, for the essential, food flavours.

The observations made on patients suffering from xerostomia indicate that these compositions are particularly effective for relieving all the symptoms associated with buccal dryness.

Other advantages and features of the present invention will appear clearly in view of the description and the Examples which follow.

DETAILED DESCRIPTION OF THE INVENTION

According to one of its essential features, the invention relates to an oily pharmaceutical composition based on peroxidised lipids and on silica, which contains, as essential constituents, peroxidised lipids which have a degree of peroxidation of between 5 and 600 milli-equivalents per kilogram, and silica which is dispersed within said peroxidised lipids at a content of greater than or equal to 0.5% by weight and less than 4% by weight with respect to the total weight of said composition.

The term "essential constituents", in the sense of the invention, is to be understood as meaning that the peroxidised lipids and the silica, in well-determined proportions, are the basic constituents of the composition which is an oily composition of well-determined viscosity. However, it will be possible for the composition of the invention to further contain other constituents which are compatible with a buccal use, such as:
- an anti-bacterial agent which is compatible with a buccal use, e.g. chlorhexidine,
- an antimycotic agent, which can be any local-use antifungal agent which is compatible with a buccal use, e.g. an imidazole-containing derivative or a contact antifungal antibiotic agent,
- an agent which improves the tolerance of the composition in the mouth, e.g. any constituent which is known as tolerance factor or as softening factor,
- a formula stabilising agent, e.g. a buffering agent, a thickening agent or fluidifying agent, or a pH corrector,
- a formula protecting agent, such as an agent having anti-bacterial effect, or a preservative, e.g. an ester of p-hydroxybenzoic acid, e.g. methyl para-hydroxybenzoate, propyl para-hydroxybenzoate, or isothiazolinone,
- a perfuming composition, e.g. a food flavour, an essential oil, an extract of a plant or of a fruit.

According to another of its essential features, the invention relates to the use of the peroxidised lipids for the preparation of a pharmaceutical composition intended for the treatment of xerostomia.

The peroxidised lipids which are used for the preparation of the compositions of the invention result from the peroxidation of unsaturated fats. The degree of peroxidation is measured according to the ISO 3960 Standard.

Peroxidised lipids which have a degree of peroxidation of between 5 and 600 milli-equivalents per kilogram, preferably between 30 and 500 milli-equivalents per kilogram, will be selected for the preparation of the compositions of the present invention.

This degree of peroxidation will more advantageously be between 50 and 300 milli-equivalents per kilogram, more preferably between 50 and 150 milli-equivalents per kilogram.

The preferred peroxidised lipids which are used according to the invention result from the peroxidation of lipids or fats of natural origin, preferably from plant origin, more preferably of lipids originating from a natural plant oil.

Sweet almond oil, hazelnut oil, groundnut oil, maize oil, grapeseed oil, sesame oil, and safflower oil, are cited as examples of natural oil selected according to the invention. It will also be possible to use a mixture of these oils.

According to a particularly preferred variant of the invention, peroxidised maize oil will be selected, and more particularly a maize oil having a degree of peroxidation of between 5 and 600 milli-equivalents per kilogram.

The peroxidised lipids which are used according to the invention are advantageously constituted, as main constituents representing in general at least 80% of the mass, of triglycerides of formula

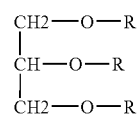

in which the radicals R are represented mainly by partially peroxidised C18 unsaturated acids (as a function of the degree of peroxidation of said lipid).

For analytical reasons which render the determination of the degree of peroxidation difficult in the compositions in the presence of silica, the compositions of the invention will often be characterised not from the degree of peroxidation of the peroxidised lipid being included in said composition, but by the content of oxidised glycerides of the composition, which content is of course directly linked to the degree of peroxidation of the peroxidised lipid which is used for the preparation.

As set forth supra, it is essential that the compositions of the invention have very specific viscosity which enables a lining, which is as complete as possible, of the buccal mucous membranes and of the tongue to be obtained upon their vaporisation as a spray in the buccal cavity by means of a dosing pump.

This specific viscosity is conferred to the composition by the presence of silica in well-determined proportions.

The compositions of the invention also contain less than 4% and at least 0.5% by weight of silica which is dispersed in the peroxidised lipid.

The preferred concentrations of silica are advantageously between 0.5 and 3.5% by weight, preferably between 0.5 and 2% by weight.

It has proved to be particularly advantageous to use qualities of silica, known as colloidal silica, i.e. silicas the diameter of the particles of which corresponds to about 1/30 of the wavelength of visible light. These are particles of amorphous silica which have diameters of about 7 to 40 nm.

Such silica particles are well-known for being able to be used for increasing the viscosity of media into which they are introduced.

An example of colloidal silica which can be used according to the present invention is the product which is marketed by the company Degussa under the trademark AEROSIL 300®.

It will nevertheless be noted that for a same concentration of silica, the viscosity of the composition depends upon the method used for the dispersion of the silica in the peroxidised oil. Further, it has appeared that the viscosity of the composition was subject to variations with time.

Under these conditions, the rheology of the compositions which are useful according to the invention will be unambiguously characterised by the viscosity of the composition upon its preparation.

Further, it is important to note that the viscosity of the composition, even if it is linked to the concentration of silica in the composition, also greatly depends upon the method used for dispersing the silica within the composition, particularly upon the agitation applied and upon the conditions of temperature during this dispersion.

Under these conditions, another way of characterising the rheology of the compositions having recourse to a feature which is more stable with time is to characterise the composition by its density.

Thus, the compositions of the invention will advantageously have, upon their preparation, a cinematic viscosity, measured in accordance with the European pharmacopoeia, by a capillary tube method at 20° C, of between 26.6 and 44.4 mm²/s.

Preferably, these compositions will also have a density of 0.95±10%.

As set forth supra, the galenic composition of the pharmaceutical composition of the present invention is particularly important since the rheology, which is characterised by the measurement of the initial viscosity and of the density of the composition, proves to be one of the essential characteristics of the composition of the invention which enables the effect sought after to be obtained.

The silica does in fact confer a certain thickening to the peroxidised oil which, due to its very specific silica content, is in a form which remains perfectly fluid conferring good distribution properties to the composition in the whole of the buccal cavity, which enables the composition to line the whole of the mucous membranes of the mouth and of the tongue, and to stay in place after vaporisation of the composition in the buccal cavity.

It is this specific viscosity which enables the peroxidised lipids to be used as a spray.

The product must in fact be sufficiently fluid to be vaporised through the vaporisation tube and pump, but sufficiently viscous to then line all the tissues of the buccal cavity.

The product of the invention is advantageously presented in a flask which is equipped with a pump device which enables the composition to be vaporised into the mouth. The quality of the pump and the diameter of the tube are selected so as to ensure a good dispersion in the form of a broken-up jet in the mouth, leading to a fine mist which then comes to line the whole of the mucous membranes of the mouth.

A pump will preferably be selected which enables dispersing, upon each press exerted, amounts of the order of 100 µL.

EXAMPLES

Unless indicated otherwise, the proportions given in the following Examples are expressed as percentages by weight.

Example 1

Buccal spray
a. Composition

| | |
|---|---|
| Peroxidised maize oil having a degree of peroxidation of between 50 and 150 milli-equivalents per kilogram | 94.4% |
| Silicon dioxide (AEROSIL 300 ® - Degussa): | 1.5% |
| Mint food flavouring: | 1.0% |
| Orange-grapefruit food flavouring: | 3.0% |
| Aspartame: | 0.1% |

The product is presented in the form of a fluid gel of yellow-golden yellow colour and has a smell of menthol and citrus fruits and a taste of mint and grapefruit.

This product has a density of the order of 0.925 and a viscosity of 35.5 mm²/s measured with the aid of a capillary tube at 20° C.

Example 2

Test of Effectiveness on Xerostomia a. Aim of the Test

The test consists of evaluating the effect of the oxidised triglycerides in users having a symptom of buccal dryness.

b. Protocol and Conditions of the Test

The product tested is sprayed into the mouth of the users in the form of a fine mist with the aid of a device equipped with a pump and a tube which disperses 100 µL at each press and the application is renewed as often as necessary. One or two sprays are made after each meal and as often as necessary and the patient rinses the mouth well before each application.

The test was carried out over a period of 15 days.

The intensity of the inconvenience caused by the dry mouth syndrome was evaluated before (time=$D_0$) and after treatment (D+15) with the aid of analogy scales of 10 cm on which each experimenter and each user notes the intensity of the inconvenience, from slight to very intense.

The test was carried out by several experimenters in free environment and more particularly in psychiatry and in cancerology and was done on 49 users 34 of which followed psychiatric or by psychotropics treatments, and 11 of which followed anti-cancer treatments by irradiation or chemotherapy.

At time $D_0$, it was established that 63.26% of the users suffered from significant to very significant symptoms.

Further, 75.51% of the users were treated beforehand with a commercial saliva substitute product whereas 24.49% of the users received no treatment before the start of the test.

c. Results Obtained by Using the Composition of Example 1 c1. Evaluation Made by the Users

The significance of the inconvenience evaluated by the user at $D_0$ on an analogical scale of 10 centimeters corresponds to an average value of 6.34.

The significance of the inconvenience evaluated by the user at D+15 on an analogical scale of 10 centimeters corresponds to an average value of 3.82.

The comparison of the average values obtained by the users at D+15 shows that 87.75% of the users were able to notice a significant improvement in their symptoms of dry mouth.

The evaluation of the decrease of the significance of the inconvenience shows an average decrease of 2.98 units on the analogical scale. The intensity of the symptoms thus decreased by 47% on average.

c2. Evaluation Made by the Experimenters

The clinical observations made by the experimenters confirm the beneficial effects reported by the users.

The experimenters did in fact attribute an average value of 6.06 to the inconvenience evaluated by the experimenter at $D_0$, on an analogical scale of 10 cm, and an average value of 3.46 to the significance of the inconvenience evaluated by the experimenter at D+15 on an analogical scale of 10 cm, and the experimenters were able to notice a significant improvement in the dry mouth syndrome in 91, 83% and an average decrease in the intensity of the symptoms of 48, 84%.

Further, a period of relief of the dry mouth syndrome was noted of more than 3 hours for 83.67% of the users, whereas the administration via the oral route or by spraying an artificial saliva only procures a transient benefit to the user.

The invention claimed is:

1. A pharmaceutical composition in the form of a non-aqueous sprayable oily fluid, the oily fluid comprising:
   peroxidized lipids which have a degree of peroxidation of between 5 and 600 milli-equivalents per kilogram, and
   silica which is dispersed within said peroxidized lipids, the oily fluid containing said silica in a concentration by weight of greater than or equal to 0.5% and less than 4%.

2. The pharmaceutical composition according to claim 1, containing 0.5 to 3.5% by weight of said silica.

3. The pharmaceutical composition according to claim 1, containing 0.5 to 2% by weight of said silica.

4. The pharmaceutical composition according to claim 1, wherein the silica is a form of colloidal silica.

5. The pharmaceutical composition according to claim 1, having a kinematic viscosity measured at 20° C. by means of a capillary viscometer, of between 26.6 and 44.4 mm²/s.

6. The pharmaceutical composition according to claim 1, having a density of 0.95 ±10%.

7. The pharmaceutical composition according to claim 1, wherein said peroxidized lipids have a degree of peroxidation of between 30 and 500 milli-equivalents per kilogram.

8. The pharmaceutical composition according to claim 1, wherein said peroxidized lipids comprise partially oxidized triglycerides of a formula:

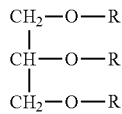

in which radicals R are partially peroxidized $C_{18}$ unsaturated acids.

9. The pharmaceutical composition according to claim 1, wherein said peroxidized lipids are obtained by peroxidation of lipids or of fats of natural origin.

10. The pharmaceutical composition according to claim 1, wherein the lipids originate from a natural plant oil.

11. The pharmaceutical composition according to claim 10, wherein the natural oil is selected from the group consisting of sweet almond oil, hazelnut oil, groundnut oil, maize oil, grapeseed oil, sesame oil, safflower oil, and mixtures thereof.

12. A method for treatment of xerostomia, comprising application by spraying in the mouth of a composition in the form of a non-aqueous oily fluid comprising peroxidized lipids having a degree of peroxidation of between 5 and 600 milli-equivalents per kilogram, said composition having a viscosity adapted for lining the buccal cavity and tongue, wherein the composition contains silica dispersed within said peroxidized lipids, the oily fluid containing said silica in a concentration by weight of greater than or equal to 0.5% and less than 4%.

13. A method according to claim 12, wherein the composition contains 0.5 to 3.5% by weight of said silica.

14. A method according to claim 13, wherein the composition contains 0.5 to 2% by weight of said silica.

15. A method according to claim 12, wherein the silica is a form of colloidal silica.

16. A method according to claim 12, wherein the composition has a kinematic viscosity measured at 20° C. by means of a capillary viscometer, of between 26.6 and 44.4 mm²/s.

17. A method according to claim 12, wherein the composition has a density of 0.95 ±10%.

18. A method according to claim 12, wherein the peroxidized lipids have a degree of peroxidation of between 30 and 500 milli-equivalents per kilogram.

19. A method according to claim 12, wherein said peroxidized lipids comprise partially oxidized triglycerides having a formula:

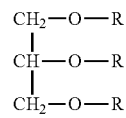

in which the radicals R are partially peroxidized $C_{18}$ unsaturated acids.

20. A method according to claim 12, wherein said peroxidized lipids are obtained by peroxidation of lipids or of fats of natural origin.

21. A method according to claim 20, wherein the lipids originate from a natural plant oil selected from the group consisting of sweet almond oil, hazelnut oil, groundnut oil, maize oil, grapeseed oil, sesame oil, safflower oil and mixtures thereof.

22. The pharmaceutical composition according to claim 1, contained in a flask comprising a pump spray device enabling the composition to be sprayed as a fine mist into the mouth of a person.

23. A non-aqueous pharmaceutical composition in the form of a sprayable oily fluid, the oily fluid comprising:
   peroxidized lipids which have a degree of peroxidation of between 5 and 600 milli-equivalents per kilogram, and
   silica which is dispersed within said peroxidized lipids, the oily fluid containing said silica in a concentration by weight of greater than or equal to 0.5% and less than 4%.

24. A pharmaceutical composition in the form of a sprayable oily fluid, the oily fluid consisting essentially of:
   peroxidized lipids which have a degree of peroxidation of between 5 and 600 milli-equivalents per kilogram,
   silica which is dispersed within said peroxidized lipids, the oily fluid containing said silica in a concentration by weight of greater than or equal to 0.5% and less than 4%, and optionally, flavoring.

25. The pharmaceutical composition according to claim 23, further comprising an anti-bacterial agent which is compatible with buccal use.

26. The composition of claim 25, wherein said anti-bacterial agent is chlorhexidine.

27. The composition of claim 23, further comprising an antimycotic agent compatible with buccal use.

28. The composition of claim 27, wherein said antimycotic agent is selected from the group consisting of an imidazole containing compound and a contact antifungal antibiotic agent.

29. The composition of claim 23, further comprising a formula stabilizing agent selected from the group consisting of a buffering agent, a thickening agent, a fludifying agent and a pH corrector.

30. The composition of claim 23, further comprising a formula protecting agent selected from the group consisting of an agent having an anti-bacterial effect and a preservative.

31. The composition of claim 30, wherein said formula protecting agent is an ester of p-hydroxybenzoic acid.

32. The composition of claim 23, further comprising a perfuming composition comprising at least one of a food flavor, an essential oil, an extract of a plant and an extract of a fruit.

33. A pharmaceutical composition consisting essentially of, by weight:

| | |
|---|---|
| peroxidized maize oil having a degree of peroxydation of between 50 and 150 milli-equivalents per kilogram | 94.4% |
| colloidal silica | 1.5% |
| Mint food flavoring | 1.0% |
| orange-grapefruit food flavoring | 3.0% |
| aspartame | 0.1%. |

* * * * *